United States Patent [19]

Cesti et al.

[11] Patent Number: 4,933,290
[45] Date of Patent: Jun. 12, 1990

[54] PROCESS FOR THE ENZYMATIC SEPARATION OF THE OPTICAL ISOMERS OF RACEMIC OXAZOLIDINONIC DERIVATIVES

[75] Inventors: Pietro Cesti, Trecate; Daniele Bianchi, Milan; Franco Francalanci, Novara; Walter Cabri, Limbiate, all of Italy

[73] Assignee: Montedison S.p.A., Milan, Italy

[21] Appl. No.: 137,721

[22] Filed: Dec. 24, 1987

[30] Foreign Application Priority Data

Dec. 30, 1986 [IT] Italy ................... 22884 A/86

[51] Int. Cl.$^5$ ............................................ C12P 41/00
[52] U.S. Cl. .................................. 435/280; 435/117; 435/120
[58] Field of Search ................... 435/280, 120

[56] References Cited

U.S. PATENT DOCUMENTS 4,588,694 5/1986 Hamaguchi et al. ............... 435/280

OTHER PUBLICATIONS

Hamaguchi et al.—Chem. Abst. vol. 104 (1986) p. 166940x.
Funda et al.—Chem. Abst. vol. 100 (1984) p. 81857t.

Primary Examiner—Sam Rosen
Attorney, Agent, or Firm—Stevens, Davis, Miller & Mosher

[57] ABSTRACT

There is disclosed a process for the biotechnological resolution, by enzymatic esterification of the corresponding racemic mixture of the S(+) and R(−) optical isomers of the oxazolidinonic compounds having formula (I):

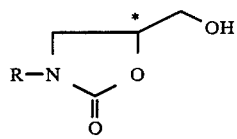

(I)

wherein R represents a, linear or branched, $C_1$-$C_8$ alkyl group, which process is characterized in that, the racemic 3-alkyl-5-hydroxymethyl-oxazolidin-2-one derivative of formula (I) is reacted with an esterifying compound, selected from esters having formula (III):

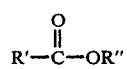

(III)

wherein R represents a, linear or branched, $C_1$-$C_{10}$ alkyl or alkenyl group, and R" represents a linear or branched, $C_1$-$C_4$ alkyl, alkenyl group, a haloalkyl (chlorine, bromine) group or a diacyl glycerolic group or from acids having formula (IV):

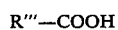

(IV)

wherein R''' represents a, linear or branched, $C_1$-$C_{20}$ alkyl or alkenyl group or from anhydrides having formula (V):

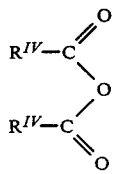

(V)

wherein $R^{IV}$ represents a, linear or branched, $C_1$-$C_6$ alkyl group, in the presence of an enzyme, immobilized on a porous carrier, capable of giving rise selectively to the esterification reaction of the R(−) isomer, while leaving the S(+) isomer substantially unchanged, which latter is then separated according to known techniques.

17 Claims, No Drawings

PROCESS FOR THE ENZYMATIC SEPARATION OF THE OPTICAL ISOMERS OF RACEMIC OXAZOLIDINONIC DERIVATIVES

DESCRIPTION OF THE INVENTION

The present invention relates to a process aiming at the separation, by enzymatic way, of the S(+) and R(−) optical isomers of racemic derivatives of oxazolidinone.

More particularly, the invention relates to a biotechnological process aiming at the separation or resolution of the optical isomers of 3-alkyl-5-hydroxymethyl-oxazolidin-2-ones, having formula (I):

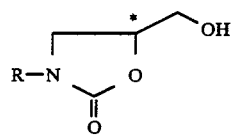

(I)

wherein R represents a, linear or branched, $C_1$-$C_8$ alkyl group, which compounds of formula (I) are usually in the form of a mixture of S(+) and R(−) optical isomers; said process being carried out in the presence of enzymes having esterase activity, coming from microorganisms or from animal tissues.

The compounds of formula (I), in the form of the S(+) and R(−) optical isomers or of their racemic mixtures, represent an important class of intermediates, which may be used advantageously in the synthesis of β-blocking drugs (Agric. Biol. Chem., 49 (1)d, 207–210, 1985), for instance according to a process, comprising the following reactions, represented schematically for the S(+) optical isomer:

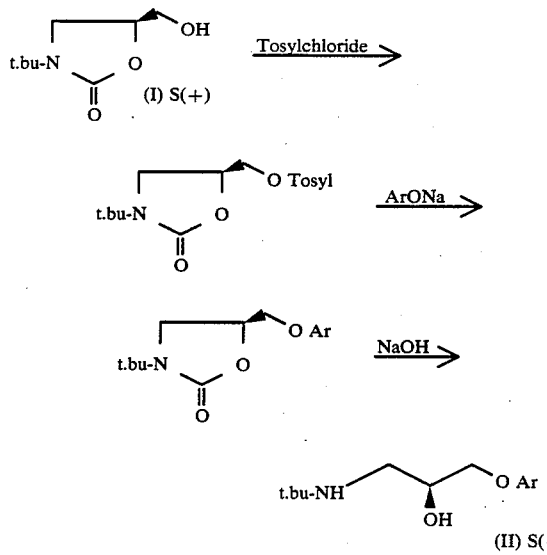

wherein Ar represents an aryl group, optionally substituted.

Thus, the compounds of formula (II) are obtained in their optically active S(−) form, which compounds form β-blocking active principles. These compounds of formula (II), however, are used in the clinical practice in the form of racemes, though the higher activity was shown of the S(−) isomer in comparison with the R(+) isomer. (Nature 210, 1336, 1966).

Therefore it stood to reason that, it was of interest to the preparer, to be able to have available an effective process for the separation of forms that are optically active, i.e. the separation of the S(+) form from the R(−) one of the racemic compound of formula (I).

On the other hand a few processes are known, concerning the synthetic selective prepartion of the compounds of formula (I) in the optically active form.

Therefore a synthesis was proposed (Chem. Pharm. Bull. 29,3593–3600, 1981; J. Org. Chem. 43, 3641, 1978) starting from D-mannitol, oxidized in the presence of Pb tetraacetate to D-glyceraldehyde acetonide, treated, in its turn, with a primary amine, yielding a 3-alkylamino-1,2-propanediol, which, finally, is cyclized into product (I) in the optically active S(+) form.

It is a matter of a method having scarse possibilities of industrial application owing to the several burdensome operating steps and owing to the employ of considerable amounts of lead tetraacetate in the first preparation step of D-glyceraldehyde acetonide from D-mannitol.

A preparation process was also described (Agr. Biol. Chem. 48, 2055-2059, 1984, European patent application E. P. 0101076) starting from a compound of formula (I) in the racemic form. Compound (I) is acetylated chemcially and then the estereal R(−) form, thus obtained, is hydrolyzed selectively by enzymatic way. Then the estereal S(+) form of the compound of formula (I) is separated and subsequently hydrolized, in its turn, by chemical way, to yield the S(+) form of compound (I).

However, this method entails also several operating steps, which do not seem to ensure sufficient advantages, particularly from an industrial point of view.

In fact, such process foresees two hydrolysis operations, one by enzymatic way and one by chemical way, besides the starting acetylation operation.

Therefore the necessity was feel to be able to have available a method, which could be carried out industrially and allowed the separation or resolution of the optical isomers of the racemic oxazolidinonic derivatives having formula (I), as defined hereinbefore, according a simple, efficient and economic operating way.

Therefore the object of the present invention is to provide a process for carrying out the separation or resolution of the optical isomers of the racemic oxazolidinonic derivatives having formula (I), by attaining directly to the S(+) isomer, that is of interest, which method, in particular, is free from the drawbacks noticed in the prior art.

The Applicant has now found that this object can be reached by operating according to a biotechnological process of enzymatic asymmetric esterification of the compounds having formula (I), starting from their recemic compounds, by using particular enzymes, endowed with selective activity, as they will defined better hereinafter.

In practice use is made of the enzymes, belonging to the lipase class, which are able to give rise to the esterification reaction stereo-selectively on the R(−) form only of the compounds having formula (I), while leaving the isomer in the S(+) form unchanged, which latter is then separated easily and utilized directly.

The object of the present invention, as defined in a more specific way, concerns a process aiming at the biotechnological separation or resolution, carried out by enzymatic esterification, of the racemic mixture of the S(+) and R(−) optical isomers of the oxalidinonic compounds having formula:

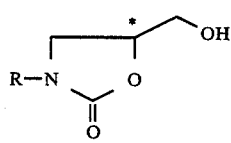
(I)

wherein R represents a, lilnear or branched, $C_1$–$C_8$ alkyl group, which process is characterized in that, the racemic 3-alkyl-5-hydroxymethyl-oxazolidin-2-one derivative of formula (I) is reacted with an esterifying compound selected from esters having formula (III).

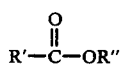
(III)

wherein R' represents a, linear or branched, $C_1$–$C_{10}$ alkyl or alkenyl group and R" represents a, linear or branched, $C_1$–$C_4$ alkyl, alkenyl group, a haloalkyl (chlorine, bromine) or a diacylglycerolic group, or from acids having formula (IV):

R'''—COOH    (IV)

wherein R''' represents a, linear or branched, $C_1$–$C_{20}$ alkyl or alkenyl group, or from anhydrides having formula (V):

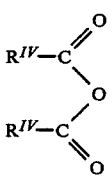
(V)

wherein $R^{IV}$ represents a, linear or branched, $C_1$–$C_6$ alkyl group, in the presence of an enzyme, immobilized on a porous carrier, capable of giving rise selectively to the esterification reaction of the R(−) isomer, while leaving the S(+) isomer of the starting racemic compound of formula (I) substantially unchanged, which latter is then separated, by operating substantially according to customary techniques.

The racemic compounds 3-alkyl-5-hydroxymethyl-oxazolidin-2-ones having formula (I), starting compounds, are known compounds and/or mayb e synthetized according to customary techniques.

According to a schematic description of the process, object of the present invention, the racemic oxazolidinonic compound, having formula (I), is reacted, in the presence of an enzyme, belonging preferably to the lipase class, in an organic solution, with a compound selected from the group comprising the esters, acids and anhydrides having formulae (III), (IV) and (V), as defined hereinbefore, respectively, according to following reactions (1), (2) and (3), given in the same sequence of the reagents above indicated.

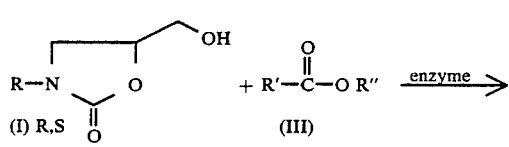
(1)

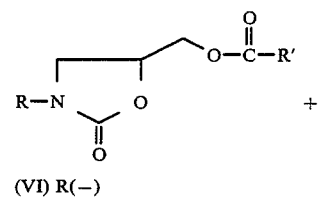
(VI) R(−)

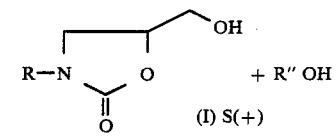
(I) S(+)

(2)

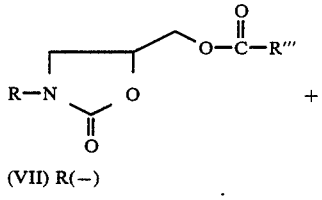
(VII) R(−)

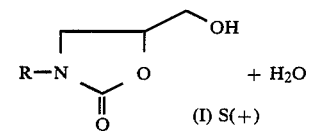
(I) S(+)

(3)

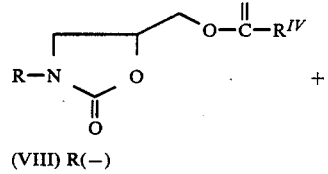
(VIII) R(−)

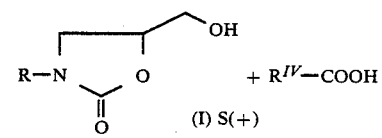
(I) S(+)

wherein symbols R, R', R", R''' and $R^{IV}$ have the meanings, as defined hereinbefore.

Referring now to the alternative of the process shown in reaction (1), we notice, it is a matter of an enzymatic transesterifications reaction, in which the starting racemic compound having formula (I) is reacted with an ester of a carboxylic acid having formula (III), in the presence of an enzyme.

The following esters having formula (III) are preferred: ethyl acetate, trichloroethyl butyrate, glycerol tributyrate (tributyrin).

One operates in the presence of an amount in excess in comparison with the stoichiometric amount of ester (III), acting in this case, besides as reagent, as solvent medium as well. In particular use is made of molar ratios ester (III)/oxazolidinonic compound (I), ranging from 10:1 and 500:1, preferably ranging from about 50:1 and 200:1.

The enzyme is employed according to a ratio by weight enzyme/compound of formula (I) ranging from about 1:1 and 1:2000.

The value of the molar concentration (M) of the oxazolidinonic compound of formula (I) in the reaction mixture can range from 0.01 M to 2M, preferably it ranges from about 0.1m to 1M.

The transesterification process is carried out by stirring strongly the reaction mixture consisting of reagent (I), ester (III), ester (III) in excess, acting as solvent and the supported enzyme, as sepcified hereinafter, at temperatures ranging from 0° to 50° C., preferably from about 20° to 30° C. The reaction time can range from about 1 to 72 hours, according to the selected operating conditions.

At the end of the reaction one starts the filtration of the solid phase consisting essentially of the immobilized enzyme, which can be recovered substantially without any loss of activity.

From the filtrate, consisting of the reaction organic phase, the S(+) 3-alkyl-5-hydroxymethyl-oxazolidin-2-one derivative is separated from the R(−) 3-alkyl-5-acyloxymethyl-oxazolidin-2-one derivative, by employing customary methods, such as column chromatography, fractional distillation or, more advantageously, by exploiting their different solubility in water and the like.

As to reaction (2), an alternative of the process object of the present invention, we note that it a matter of a reaction of enzymatic esterification, in which the starting racemic compound having formula (I) is reacted with a carboxylic acid having formula (IV), in the presence of an enzyme.

The following acids having formula (IV) are preferred: octanoic acid, decanoic acid and lauric acid.

One operates in an organic solvent, preferably selected from the aromatic hydrocarbons (for instance benzene, toluene and the like) and the halogenated aliphatic hydrocarbons (methylene chloride, chloroform and the like).

In the reaction use is made of molar ratios acid (IV)/oxazolidinonic compound (I) ranging from 0.6:1 to 5:1, preferably ranging from about 0.8:1 to 1.5:1.

The enzyme is employed according to a ratio by weight enzyme/compound of formula (I) ranging from about 1:1 to 1:2000.

The value of the molar concentration (M) of the oxazolidinonic compound of formula (I) in the reaction mixture can range from 0.01M to 2M, preferably it ranges from about 0.1M to 1M, according to compound (I), that has been used.

Finally one operates by stirring strongly the reaction mixture and by carrying on under the parametric conditions, as described with regard to the process alternative concerning the above-mentioned reaction (1).

The process alternative shown in reaction (3), according to the present invention, also consists in an enzymatic esterification reaction via anhydrides, in which reaction the starting racemic compound, having formula (I), is reacted with an anhydride of a carboxylic acid having formula (V), in the presence of an enzyme.

The following anhydrides are preferred: acetic anhydride and propionic anhydride.

One operates in an organic solvent, selected preferably from aromatic hydrocarbons and halogenated aliphatic hydrocarbons, as described with regard to the process alternative concerning reaction (2).

Likewise as in aforesaid alternative (2), use is made in the reaction of molar ratios anhydrides (V)/oxazolidinonic compound (I) ranging from 0.6:1 to 5:1, preferably such molar ratios range from about 0.8:1 to 1.5:1 and the enzyme is employed according to a ratio by weight enzyme/compound of formula (I) ranging from about 1:1 to 1:2000.

The value of the molar concentration of the oxazolidinonic compound of formula (I) in the reaction mixture can range from about 0.01M to 2M, it ranges preferably from about 0.1 and 1M, according to compound (I), that has been used.

The esterification process is carried out by stirring strongly the reaction mixture consisting of reagent (I), reagent (V), the solvent and the supported enzyme, at temperatures ranging from −10° to 30° C., preferably from about 0° to 20° C. The reaction time can range from about 10 minutes to 24 hours, according to the selected operating conditions.

At the end of the reaction, after having removed the excess of anhydride (V) by means of an aqueous solution of an alkaline carbonate, one carries on under the conditions, described hereinbefore, relating to the process alternative concerning reaction (1).

For carrying out the process, object of the present invention, use can be made of enzymes having hydrolytic action, which can be found on the market, having different origin, coming from microorganisms or animal tissues, preferably belonging to the lipase class.

Among these enzymes, the following ones, as defined hereinafter, proved to be particularly active:

| Enzyme | Origin | Manufacturer |
| --- | --- | --- |
| LPL | *Pseudomonas Aeruginosa* | Amano. Pharm. Co. (Japan) |
| LIPASE P | *Pseudomonas Fluorescens* | Amano. Pharm. Co. (Japan) |
| LIPASE | *Chromobacterium Viscosum* | Toyobo (Japan) |
| LIPASE PL 266 | Alcaligenes | Meito Sangyo Co. (Japan) |
| CHOLESTEROL ESTERASE | Pseudomonas sp. | Toyobo (Japan) |
| STEAPSIN | Porcine Pancreas | Sigma Chem. Co. (USA) |
| PANCREATIN | Porcine Pancreas | Unibios (Italy) |

The following enzyme are mostly preferred: LPL, LIPASE P, LIPASE from *Chromobacterium Viscosum*, LIPASE PL 266.

According to the present invention, the enzymes for the use are immobilized on suitable carriers or substrates in order to increase their stability and to facilitate their recovery and further utilization.

Porous carriers having a high surface area proved to be particularly suitable to this purpose, such as diatomaceous earths, alumina, silica, acrylic resins, polystyrenic resins and phenol-formalydehyde resins. The immobilization can be carried out easily, by letting absorb an aqueous buffer solution containing the enzyme on the porous carrier and then by drying said carrier and so on.

The process, on account of its simple and gentle operating conditions, proves to be particularly advantageous. A particular aspect of high interest consists in the possibility of operating according to an one-step process, leading to the direct separation of the desired S(+) form from the R(−) one, with high yields and purity degree.

The following examples will now illustrate the invention, by way of illustration and not of limitation.

EXAMPLE 1

Enzyme immobilization 25 mg of enzyme L.P.L. Amano 100S (lipoprotein lipase EC 3.1.1.4, from *Pseudomonas aeruginosa*; Amano Pharmaceutical Co., Ltd; 1.120 units per mg) dissolved in 3 ml of a buffer solution Na/K phosphate 0.1 N at pH=7, were added to 500 mg of celite 577 (Johns—Manville Ltd. Richmond, Surrey).

The mixture, thus obtained, was stirred, in order to obtain a uniform distribution of the enzymes, afterwards it was dried in the air at 20° C. over 24 hours.

Transesterification reaction

Separation of the R(−) and S(+) isomers of 3-terbutyl-5-hydroxymethyl oxazolidin-2-one.

5 g of (R)(S)-3-terbutyl-5-hydroxymethyl oxazolidin-2-one and 500 mg of celite containing the immobilized enzyme, were added to 200 ml of ethyl acetate.

The mixture was stirred strongly at 20° C. and the reaction was checked by gaschromatography.

After 6 hours (50% conversion) the enzyme was recovered by filtration and ethyl acetate was evaporated at reduced pressure.

Then the residue was analyzed by chromatography on a silica gel column, by eluting with a mixture ethyl acetate-hexane 7:3.

Thus one obtained 2.8 g of (R)-(−)-3-terbutyl-5-acetoxymethyloxazolidin-2-one, as a colourless oil with $[\alpha]_D^{16} = -36.2°$-(C=1.0, CHCl$_3$), $^1$H-NMR (90MHz in CDCl$_3$) δ(ppm): 1.4 (9H, s, (CH$_3$)$_3$C—), 2.2(3H, s, CH$_3$CO—), 3.35~3.85 (2H, m, —CH$_2$N—), 4.1~4.25(2H, m, CH$_2$O—), 4.45~4.75(1H, m, CH$_2$CH(O—)CH$_2$); and 2.3 g of S-(+)-3-terbutyl-5-hydroxymethyloxazolidin-2-one, as a white solid with $[\alpha]_D^{16}+46.0°$ (C=1, CHCl$_3$), (after crystallization from ethyl acetate-hexane 1:1), $^1$H-NMR(90MHz in CDCl$_3$) δ(ppm): 1.4 (9H, s, (CH$_3$)$_3$C—), 3.4~3.95(5H, m, —CH$_2$N—, —CH$_2$O—, —OH), 4.3~4.6(1H, m, —CH$_2$CH(O—)CH$_2$).

(R)-(−)-3-terbutyl-5-acetoxymethyloxazolidin-2-one, thus obtained, was hydrolyzed at pH 12 by means of aqueous sodium hydroxide.

On completion of the hydrolysis the mixture was extracted by means of 50 ml of ethyl acetate, the organic phase was dehydrated and the solvent was evaporated at reduced pressure. 2.2 g of R-(−)-3-terbutyl-5-hydroxymethyloxazolidin-2-one were thus obtained, as a white solid with $[\alpha]_D^{16}-45.9°$ after crystallization.

Enzyme recycle

The recovered enzyme was used again for further two consecutive cycles under the same conditions, as described hereinbefore, without noticing any appreciable activity loss.

EXAMPLES 2-11

The procedure of example 1 was repeated, while changing the ester used for the transesterification, the enzyme and the inert carrier.

The results are set forth in enclosed Table 1.

EXAMPLE 12

Transesterification reaction

Separation of the R(−) and S(+) enantiomers of 3-isopropyl-5-hydroxymethyloxazolidin-2-one.

5 g of 3-isopropyl-5-hydroxymethyloxazolidin-2-one and 1 g of celite 577 containing 250 mg of enzyme Lipase P (from *Pseudomonas Fluorescens*, Amano Pharmaceutical Co., Ltd., 30 units per mg), immobilized according to the same procedure, as described in Example 1, were added to 200 ml of 2,2,2-trichloroethylbutyrate.

The mixture was stirred strongly at 20° C. over 6 hours (50% conversion), afterwards it was processed likewise as described in example 1.

One obtained 3.4 g of R(−)-3-isopropyl-5-butyryloxymethyloxazolidin-2-one, as a colourless oil, $^1$H-NMR (90MHz in CDCl$_3$) δ(ppm): 0.75~2.5 (13H, m, C$_3$H$_7$—, (CH$_3$)$_2$CH—), 3.2~4.85(6H, m, —CH$_2$N—, CH$_2$O—, (CH$_3$)$_2$CH—, —CH$_2$CH(O—)CH$_2$—), and 2.4 g of S-(+)-3-isopropyl-5-hydroxymethyloxazolidin-2-one, as a white solid with $[\alpha]_D^{20}+55.3°$ (C=1, in CHCl$_3$), after crystallization from hexane-ethyl acetate 1:1, $^1$M-NHR, (90MHz in CDCl$_3$) δ(ppm): 1.2 (6H, d, —CH(CH$_3$)$_2$), 3.4~4.2 (6H, m, —CH$_2$N—, —CH$_2$O—, (CH$_3$)$_2$CH, —OH), 4.3~4.7(1H, m, —CH$_2$CH(O—)CH$_2$—).

By hydrolyzing with aqueous sodium hydroxide the (R)-(−)-3-isopropyl-5-butyryloxymethyloxazolidin-2-one, thus isolated, 2.3 g of R-(−)-3-isopropyl-5-hydroxymethyloxazolidin-2-one were obtained, as a white solid with $[\alpha]_D^{20}-55.3°$ (C=1, in CHCl$_3$) after crystallization.

EXAMPLES 13-18

The procedure of example 12 was repeated, while changing the ester used for the transesterification, the enzyme and the inert carrier.

The results are set forth in enclosed Table II.

EXAMPLE 19

Esterification reaction

Separation of the R(−) and S(+) enantiomers of 3-terbutyl-5-hydroxymethyloxazolidin-2-one.

5 g of 3-terbutyl-5-hydroxymethyloxazolidin-2-one, 4.1 g of n-octanoic acid and 25 mg of enzyme LPL immobilized on 500 mg of celite 577, according to the same procedure as described in example 1, were added to 100 ml of benzene.

The mixture was stirred strongly at 20° C. and the reaction was checked by gas-chromatography.

After 24 hours (48% conversion) the enzyme was recovered by filtration and benzene was evaporated at reduced pressure.

The residue was analysed by chromatography on silica gel column, by eluting with a mixture ethyl acetate-hexane 7:3.

Thus one obtained 4 g of R-(−)-3-terbutyl-5-octanoyloxymethyloxazolidin-2-one, as a colourless oil, $^1$H-NMR(90MHz in CDCl$_3$) δ(ppm): 0.7~0.25 (24H, m, C$_7$H$_{15}$, (CH$_3$)$_3$C), 3.3~3.85 (2H, m, —CH$_2$N—), 4.15~4.3(2H, m, —CH$_2$O—), 4.45~4.75(1H, m, CH₂CH(O)CH₂—); and 2.4 g di S-(+)-3-terbutyl-5-hydroxymethyloxazolidin-2-one, as a white solid with $[\alpha]_D^{20}+45.7°$ (C=1 in CHCl₃) after crystallization from hexane-ethyl acetate 1:1.

By hydrolyzing with aqueous sodium hydroxide the R-(−)-3-terbutyl-5-octanoyloxymethyloxazolidin-2-one, thus isolated, one obtained 2,1 g of R-(−)-3-terbutyl-5-hydroxymethyloxazolidin-2-one, as a white solid, with $[\alpha]_D^{20}-45.1°$ (C=1 in CHCl₃) after crystallization.

EXAMPLES 20–25

The procedure of example 19 was repeated, while changing the acid used for the esterification, the enzyme and the inert carrier.

The results are set forth in enclosed Table III.

EXAMPLE 26

Esterification reaction

Separation of the R(−) and S(+) enantiomers of 3-isopropyl-5-hydroxymethyloxazolidin-2-one 5 g of 3-isopropyl-5-hydroxymethyloxazolidin-2-one, 4 g of octanoic acid and 250 mg of lipase P, immobilized on 1 g of celite 577 according to the same procedure described in example 1, were added to 100 ml of benzene.

The mixture was stirred strongly at 20° C. and the reaction was checked by chromatographic methods.

After 24 hours (about 50% conversion) the enzyme was recovered by filtration and benzene was evaporated at reduced pressure.

The residue was analysed by chromatography on silica gel column, by eluting with a mixture of ethyl acetate-hexane 7:3.

Thus one obtained 4.0 g of R(−)-3-isopropyl-5-octanoyloxymethyloxazolidin-2-one, as a colourless oil, ¹H-NMR (90M-M₂ in CDCl₃) δ(ppm): 0.75∼2.5(21H, m, C₇H₁₃, (CH₃)₂CH—), 3.2∼3.75(2H, m, —CH₂N—), 3.95∼4.4(3H, m, —CH₂O—, (CH₃)₂CH—), 4.55∼4.85(1H, m, —CH₂CH(O—)CH₂—); and 2.3 g of S-(+)-3-isopropyl-5-hydroxymethyloxazolidin-2-one, as a white solid with $[\alpha]_D^{20}+55.4°$ (C=1 in CHCl₃) after crystallization from hexane ethyl acetate 1:1.

By hydrolyzing with aqueous sodium hydrate the R-(−)-3-isopropyl-5-octanoyloxymethyloxazolidin-2-one, thus isolated, one obtained 2 g of R-(−)-3-isopropyl-5-hydroxymethyloxazolidin-2-one, as a white solid with $[\alpha]_D^{20}-55.3°$ after crystallization.

EXAMPLES 27–30

The procedure of example 26 was repeated, while changing the acid used for the esterification, the enzyme and the inert carrier.

The results are set forth in enclosed Table IV.

EXAMPLE 31

Esterification reaction by means of anhydrides

Separation of the R(−) and S(+) enantiomers of 3-terbutyl-5-hydroxymethyloxazolidin-2-one.

5 g of 3-terbutyl-5-hydroxymethyloxazolidin-2-one, 25 mg of enzyme LPL immobilized on 500 mg of celite 577, according to the same procedure of example 1, and 2 g of acetic anhydride were added 100 ml of methylene chloride.

The mixture was stirred strongly and the reaction was checked by chromatographic methods.

After 3 hours (50% conversion) the enzyme was recovered by filtration.

The solution was washed with a solution saturated with sodium carbonate.

Then methylene chloride was dehydrated on sodium sulphate and evaporated at reduced pressure.

The residue was analysed by chromatography on silica gel column, by eluting with ethyl acetate-hexane 7:3.

One obtained 2.8 g of R(−)-3-terbutyl-5-acetoxymethyloxazolidin-2-one, as a colourless oil and 2.4 g of S(+)-3-terbutyl-5-hydroxymethyloxazolidin-2-one, as a white solid with $[\alpha]_D^{20}$ (C=1, in CHCl₃)+45.9° after crystallization from ethyl acetate-hexane 1:1.

By hydrolyzing with aqueous sodium hydroxide the R-(−)-3-terbutyl-5-acetoxymethyloxazolidin-2-one, thus isolated, one obtained 2 g of R-(−)-3-terbutyl-5-hydroxymethyloxazolidin-2-one, as a white solid with $[\alpha]_D^{20}$ (C=1, CHCl₃)−46.0° after crystallization.

EXAMPLE 32

Esterification reaction by means of anhydrides

Separation of the R(−) and S(+) enantiomers of 3-isopropyl-5-hydroxymethyloxazolidin-2-one.

5 g of 3-isopropyl-5-hydroxymethyloxazolidin-2-one, 250 mg of Lipase P immobilized on 1 g of celite 577, according to the procedure described in example 1, and 2.6 g of acetic anhydride were added to 100 ml of benzene.

The mixture was stirred strongly and the reaction was checked by chromatographic methods.

After 3 hours (48% conversion) the enzyme was recovered by filtration.

The solution in benzene—was washed with a solution saturated with sodium carbonate, dehydrated on sodium sulphate and the solvent was evaporated at reduced pressure.

The residue was analysed by chromatography on silica gel column, by eluting with ethyl acetate-hexane 7:3.

One obtained 2.7 g of R-(−)-3-isopropyl-5-acetoxymethyloxazolidin-2-one, as an colourless liquid and 2.2 g of S-(+)-3-isopropyl-5-hydroxymethyloxazolidin-2-one, as a white solid, with $[\alpha]_D^{20}$ (C=1 in CHCl₃)+55.4° after crystallization from hexane/ethylacetate 1:1.

By hydrolyzing with aqueous sodium hydroxide the R(−)-3-isopropyl-5-acetoxymethyloxazolidin-2-one, thus isolated, one obtained 2 g of R-(−)-3-isopropyl-5-hydroxymethyloxazolidin-2-one, as a white solid with $[\alpha]_D^{20}$ (C=1, in CHCl₃) −54.2° after crystallization.

TABLE I

| EX-AMPLE | ENZYME | CARRIER | ESTER | % CONVERSION | S(+) structure $[\alpha]_D^{20}$ (C = 1, CHCl$_3$) | R(−) structure $[\alpha]_D^{20}$ (C = 1, CHCl$_3$) |
|---|---|---|---|---|---|---|
| 2 | LPL | CROMOSORB 101 | ETHYL PROPIONATE | 50% | +46,0 | −45,9 |
| 3 | LPL | AMBERLITE XAD 7 | TRIBUTYRIN | 48% | +45,8 | −45,9 |
| 4 | LIPASE P | CELITE 577 | ETHYL ACETATE | 49% | +45,8 | −45,8 |
| 5 | LIPASE P | CELITE 577 | ETHYL ACETATE | 30% | +19,7 | −46,0 |
| 6 | LIPASE P | CROMOSORB 101 | ETHYL HEXANOATE | 48% | +45,0 | −45,7 |
| 7 | LIPASE FROM CROMOBACTERIUM VISCOSUM | CELITE 577 | ETHYL ACETATE | 50% | +45,3 | −45,7 |
| 9 | LIPASE FROM CROMOBACTERIUM VISCOSUM | CELITE 577 | TRICHLOROETHYL BUTYRATE | 50% | +46,0 | −45,9 |
| 10 | PPL | CELITE 577 | ETHYL ACETATE | 30% | +12,7 | −30,2 |
| 11 | COLESTEROL ESTERASE FROM PSEUDOMONAS | CELITE 577 | ETHYL ACETATE | 70% | +22,3 | −11,7 |

TABLE II

| EX-AMPLE | ENZYME | CARRIER | ESTER | % CONVERSION | S(+) structure $[\alpha]_D^{20}$ (C = 1, CHCl$_3$) | R(−) structure $[\alpha]_D^{20}$ (C = 1, CHCl$_3$) |
|---|---|---|---|---|---|---|
| 13 | LPL | CELITE 577 | ETHYL ACETATE | 50% | +55,4 | −55,3 |
| 14 | LPL | CELITE 577 | TRICHLOROETHYL BUTYRATE | 45% | +53,0 | −55,4 |
| 15 | LIPASE P | AMBERLITE XAD 7 | ETHYL ACETATE | 43% | +50,0 | −55,1 |
| 16 | LIPASE P | CROMOSORB 101 | TRIBUTYRIN | 49% | +55,2 | −55,2 |
| 17 | LIPASE FROM CROMOBACTERIUM VISCOSUM | CROMOSORB 101 | ETHYL HEXANOATE | 50% | +55,2 | −55,3 |
| 18 | COLESTEROL ESTERASE FROM PSEUDOMONAS | CELITE 577 | ETHYL ACETATE | 50% | +22,1 | −19,5 |

TABLE III

| EXAMPLE | ENZYME | CARRIER | ACID | % CONVERSION | S(+) structure $[\alpha]_D^{20}$ (C = 1, CHCl$_3$) | R(−) structure $[\alpha]_D^{20}$ (C = 1, CHCl$_3$) |
|---|---|---|---|---|---|---|
| 20 | LPL | CROMOSORB 101 | N OCTANOIC ACID | 48% | +45,8 | −45,6 |
| 21 | LIPASE P | CELITE 577 | N OCTANOIC ACID | 45% | +43,2 | −45,7 |
| 22 | LPL | CELITE 577 | N DECANOIC ACID | 49% | +45,9 | −45,8 |
| 23 | LIPASE FROM CROMOBACTERIUM VISCOSUM | CELITE 577 | N DECANOIC ACID | 50% | +45,6 | −45,5 |
| 24 | LPL | CELITE 577 | LAURIC ACID | 47% | +44,2 | −45,7 |
| 25 | LIPASE P | AMBERLITE | LAURIC ACID | 47% | +44,6 | −45,8 |

TABLE III-continued

| | | | | % CON-VER-SION | $[\alpha]_D^{20}$ (C = 1,CHCl$_3$) S(+) isomer | $[\alpha]_D^{20}$ (C = 1,CHCl$_3$) R(−) isomer |
|---|---|---|---|---|---|---|
| EXAMPLE | ENZYME | CARRIER | ACID | | | |
| | | XAD 7 | | | | |

TABLE IV

| | | | | % CON-VER-SION | $[\alpha]_D^{20}$ (C = 1,CHCl$_3$) S(+) isomer | $[\alpha]_D^{20}$ (C = 1,CHCl$_3$) R(−) isomer |
|---|---|---|---|---|---|---|
| EXAMPLE | ENZYME | CARRIER | ACID | | | |
| 27 | LPL | CELITE 577 | N—OCTANOIC ACID | 50% | +55,4 | −55,3 |
| 28 | LIPASE P | CELITE 577 | N—DECANOIC ACID | 45% | +54,0 | −55,2 |
| 29 | LPL | AMBERLITE XAD 7 | LAURIC ACID | 48% | +54,7 | −55,1 |
| 30 | LIPASE P | CELITE 577 | LAURIC ACID | 49% | +55,1 | −55,3 |

We claim:

1. A process for the biotechnological separation by enzymatic esterification of the racemic mixture of the S(+) and R(−) optical isomers of oxazolidinonic compounds having the formula (I):

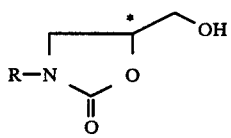     (I)

wherein R represents a linear or branched C$_1$–C$_8$ alkyl group, which process is characterized in that the racemic 3-alkyl-5-hydroxy-methyl-oxazolidin-2-one derivative of formula (I) is reacted with an ester having the formula (III):

     (III)

wherein R' represents a linear or branched C$_1$–C$_{10}$ alkyl or alkenyl group and R" represents a linear or branched C$_1$–C$_4$ alkyl, alkenyl group, a haloalkyl group or a diacylglycerolic group, or with an acid having the formula (IV):

     (IV)

wherein R''' represents a linear or branched C$_1$–C$_{20}$ alkyl or alkenyl group, or with an anhydride having the formula (V):

     (V)

wherein R$^{IV}$ represents a linear or branched C$_1$–C$_6$ alkyl group, in the presence of an enzyme of the lipase class immobilized on a porous carrier, capable of giving rise selectively to the esterification reaction of the R(−) isomer, while leaving the S(+) isomer of the racemic starting compound of formula (I) substantially unchanged, which latter is then separated.

2. A process according to claim 1, characterized in that said process is carried out by using an ester of a carboxylic acid having the formula (III), in an amount in excess of the stoichiometric amount, ranging from about 10:1 to 500:1 moles with respect to the oxazolidinonic compound having the formula (I).

3. A process according to claim 2, characterized in that the ester of the carboxylic acid having the formula (III) is used in an amount ranging from about 50:1 to 200:1 moles with respect to the oxazolidinonic compound having the formula (I).

4. A process according to claim 1, 2 or 3, characterized in that said process is carried out at temperatures ranging from about 0° to 50° C.

5. A process according to claim 4, characterized in that said process is carried out at temperatures ranging from about 20° to 30° C.

6. A process according to claim 1, characterized in that said process is carried out by using a carboxylic acid of the formula (IV) or an anhydride of the formula (V), in a molar ratio of the carboxylic acid having the formula (IV) or, respectively, of the anhydride of the carboxylic acid having formula (V), with respect to the starting oxazolidinonic compound of the formula (I), ranging from about 0.6:1 to 5:1.

7. A process according to claim 6, characterized in that said process is carried out by using a molar ratio of the carboxylic acid having the formula (IV) or, respectively, of the anhydride of the carboxylic acid having the formula (V), with respect to the starting oxazolidinonic compound of the formula (I), ranging from about 0.8:1 to 1.5:1.

8. A process according to claim 1, 6 or 7, characterized in that the reaction with the acid having the formula (IV) or with the anhydride having the formula (V) is carried out in an organic solvent selected from the class consisting of aromatic hydrocarbons and halogenated aliphatic hydrocarbons.

9. A process according to claim 8, characterized in that the solvent is selected from the class consisting of benzene, toluene, methylene chloride, and chloroform.

10. A process according to claim 1, 6, 7 or 9, characterized in that an acid having the formula (IV) is used and the reaction is carried out at temperatures ranging from about 0° to 50° C.

11. A process according to claim 10, characterized in that the reaction is carried out at temperatures ranging from about 20° to 30° C.

12. A process according to claim 1, 6, 7 or 9, characterized in that an anhydride having the formula (V) is used and the reaction is carried out at temperatures ranging from about −10° to 30° C.

13. A process according to claim 12, characterized in that the reaction is carried out at temperatures ranging from about 0° to 20° C.

14. A process according to claim 1, 2 or 3, characterized in that the molar concentration of the oxazolidinonic compound having the formula (I) in the reaction mixture ranges from about 0.01 to 2 moles.

15. A process according to claim 1, 2 or 3, characterized in that the molar concentration of the oxazolidinonic compound having the formula (I) in the reaction mixture ranges from about 0.1 to 1 mole.

16. A process according to claim 1, 2 or 3, characterized in that the enzyme consists of a lipase selected from the class consisting of LPL, LIPASE P, lipase from *Chromobacterium viscosum*, and LIPASE PL 266.

17. A process according to claim 1, 2 or 3, characterized in that the ratios by weight enzyme/compound having the formula (I) range from about 1:1 to 1:2000.

* * * * *